United States Patent

Miyaoka et al.

Patent Number: 5,225,426
Date of Patent: Jul. 6, 1993

[54] THIAZOLIDINE-2,4-DIONE COMOUND AND METHOD OF TREATMENT OF DIABETIC COMPLICATIONS

[75] Inventors: Shozo Miyaoka; Hiroaki Takahashi; Hideto Ushijima; Hiroko Sato, all of Ashigarakami, Japan

[73] Assignee: Terumo Kabushiki Kaisha, Tokyo, Japan

[21] Appl. No.: 802,308

[22] Filed: Dec. 4, 1991

[30] Foreign Application Priority Data

Dec. 6, 1990 [JP] Japan .................................. 2-413602

[51] Int. Cl.$^5$ ............................................. A61K 31/425
[52] U.S. Cl. ....................................... 514/369; 548/183
[58] Field of Search ........................... 548/183; 514/369

[56] References Cited

U.S. PATENT DOCUMENTS

| | | | |
|---|---|---|---|
| 4,340,605 | 7/1982 | Kawamatsu et al. | 548/183 |
| 4,725,610 | 2/1988 | Meguro et al. | 548/183 |
| 4,948,900 | 8/1990 | Iijima et al. | 548/183 |
| 5,061,717 | 10/1991 | Clark et al. | 514/342 |

FOREIGN PATENT DOCUMENTS

| | | |
|---|---|---|
| 0117035 | 1/1984 | European Pat. Off. . |
| 0332331 | 9/1987 | European Pat. Off. . |
| 64-113019 | 1/1989 | Japan . |

OTHER PUBLICATIONS

Chemical Abstract vol. III, No. 23, Abstract No. 214230 to Chin et al.

Primary Examiner—Joseph Paul Brust
Assistant Examiner—Mary Susan H. Gabilan
Attorney, Agent, or Firm—Burns, Doane, Swecker & Mathis

[57] ABSTRACT

A novel compound is proposed which is effective in curing various complications as with catarat, retinopathy, neurotic disorder, and renal disorder. The thiazolidine-2,4-dione compound represented by the following general formula I combines an action to inhibit aldose reductase and an action to depress blood sugar and manifests an efficacy in the cure of various complications as with catarat, retinopathy, neurotic diorder, and renal disorder.

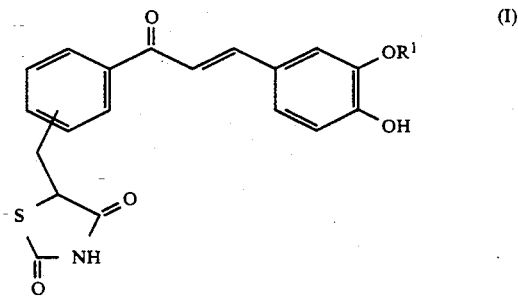

wherein $R^1$ is a hydrogen atom or a methyl group.

7 Claims, No Drawings

THIAZOLIDINE-2,4-DIONE COMOUND AND METHOD OF TREATMENT OF DIABETIC COMPLICATIONS

BACKGROUND OF THE INVENTION

1. Field of the Invention

This invention relates to a novel thiazolidine-2,4-dione compound, a method for the production thereof, and a medicine containing the compound for the cure of diabetic complications. More particularly, it relates to a novel thiazolidine-2,4-dione compound combining an aldose reductase inhibiting action and a blood sugar depressing action which are useful for the cure of various complicated diseases involving cataract, retinopathy, neurotic disorder(neuropathy), and renal disorder(nephropathy).

2. Description of the Prior Art

The complex abnormality of various metabolisms induced by the deficiency in the action of insulin has no negligible participation in the onset of cataract, retinopathy, neurotic disorder, and renal disorder complicated with diabetes. The polyol path occupies a large proportion to all the metabolic paths of interest and the participation of this particular path is thought to be very logical. This polyol path consists in effecting the metabolism of an aldose such as glucose or galactose into a ketose such as fructose via a polyol such as sorbitol or galactose, for example.

In the diabetic patients, this polyol path exists in an advanced state and the consequent cellular accumulation of sorbitol is regarded as a problem. The enzyme which catalyzes the conversion of aldose to polyol as the first step in the polyol path is called an aldose reductase. It is thought to constitute the velocity-controlling enzyme of this path. It has been reported that a measure to inhibit the action of this aldose reductate and decelerate the production and accumulation of sorbitol is effective in curing various complications of diabetes. Thus, efforts have been extensively devoted to the development of medicines which inhibit the action of aldose reductase.

Thiazolidine dione compounds of a certain sort have been heretofore known as a blood sugar depressant EP-A-0 332 331. It has not yet been known that these compounds are possessed of an action to inhibit an aldose reductase.

Though the aldose reductase inhibiting agents which have been heretofore known to the art indeed are capable of decelerating the production and accumulation of sorbitol, they are devoid of an action to correct the state of high blood sugar which is the basic cause for diabetic complications. Thus, they are prominently effective in curing cataract and neurotic disorder which are thought to bear heavily on the polyol path and yet fail to manifest any conspicuous effect in curing renal disorder and retinopathy whose causes defy unique elucidation. In the circumstances, therefore, an earnest desire has been expressed for the development of a medicine which combines the action of inhibiting an aldose reductase and the action of depressing blood sugar and manifests an extensive effect in the cure of various diabetic complications.

An object of this invention, therefore, is to provide a novel thiazolidine-2,4-dione compound, a method for the production thereof, and a medicine containing the compound and used for the cure of diabetic complications.

Another object of this invention is to provide a medicine which combines an aldose reductase inhibiting action and a blood sugar depressing action and manifests an extensive effect in the cure of various diabetic complications.

SUMMARY OF THE INVENTION

The objects described above are accomplished by a thiazolidine-2,4-dione compound represented by the general formula I:

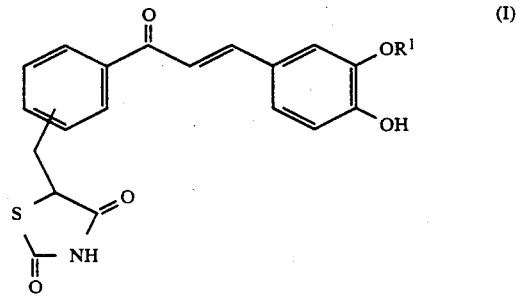

wherein $R^1$ is a hydrogen atom or a methyl group.

The objects are accomplished by a method for the production of a thiazolidine-2,4-dione compound represented by the general formula I:

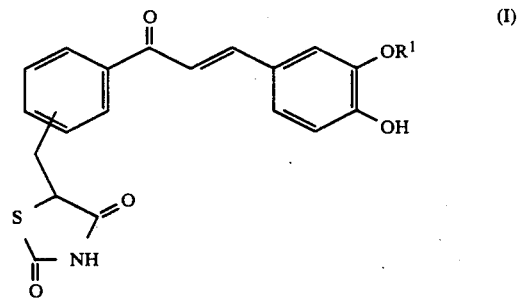

wherein $R^1$ is a hydrogen atom or a methyl group, by causing a thiazolidine compound represented by the formula II:

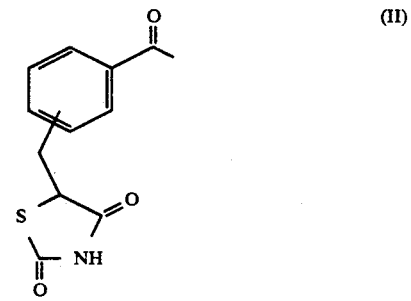

to react with a benzaldehyde compound represented by the general formula III:

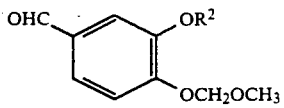

(III)

wherein $R^2$ is a methyl group when $R^1$ is a methyl group or a methoxymethyl group when $R^1$ is a hydrogen atom, in the presence of a base and subjecting the methoxymethyl group of the resultant reaction product to a reaction for denuding(deprotecting) the methoxymethyl group of protection.

The objects are further accomplished by a medicine which has as an active component thereof a thiazolidine-2,4-dione compound represented by the general formula I mentioned above and is used for the cure of diabetic complications.

The objects are further accomplished by a pharmaceutical composition for diabetic complications, which the pharmaceutical composition comprises a thiazolidine-2,4-dione compound represented by the general formula I mentioned above and a pharmaceutically acceptable carrier.

EXPLANATION OF THE PREFERRED EMBODIMENT

The thiazolidine-2,4-dione compound contemplated by the present invention is a novel compound represented by the general formula I, wherein $R^1$ is a hydrogen atom or a methyl group. Representative examples of this compound are 5-{4-[3-(3,4-dihydroxyphenyl)-2-propenoyl]benzyl}thiazolidine-2,4-dione, 5-{4-[3-(4-hydroxy-3-methoxyphenyl)- 2propenoyl]benzyl} thiazolidine-2,4-dione, 5-{3-[3-(3,4-dihydroxyphenyl)-2-propenoyl]benzyl}thiazolidine-2,4-dione, 5-{3-[3-(4-hydroxy-3-methoxyphenyl)-2-propenoyl]benzyl} thiazolidine-2,4-dione, 5-{2-[3-(3,4-dihydroxyphenyl)-2-propenoyl]benzyl}thiazolidine-2,4-dione, and 5-{2-[3-(4-hydroxy- 3-methoxyphenyl)-2-propenoyl]benzyl} thiazolidine-2, 4-dione.

The thiazolidine-2,4-dione compound represented by the general formula I is produced by causing a thiazolidine compound represented by the formula II to react with a benzaldehyde compound represented by the general formula III in the presence of a base, preferably in an organic solvent, and subjecting the methoxymethyl group of the resultant reaction product to a reaction for deprotecting the methoxymethyl group of protection.

For use in the reaction mentioned above, the amount of the benzaldehyde compound represented by the general formula III is in the range of from 1 to 3 mols, preferably from 1 to 1.2 mols, per mol of the thiazolidine compound represented by the formula II. This reaction is carried out with the reactants kept stirred at a temperature in the range of from 20° to 80° C., preferably from 25° to 30° C., for a period in the range of from 5 to 24 hours, preferably from 5 to 10 hours. The bases which are usable for this reaction include sodium hydroxide, potassium hydroxide, lithium hydroxide, for example. The amount of the base to be used is in the range of from 200 to 300% by weight, preferably from 250 to 300% by weight, based on the amount of the thiazolidine compound represented by the formula II. The organic solvents which are usable in the reaction include methanol, ethanol, isopropanol, butanols, ethylene glycol, ethylene glycol monoethyl ether, and ethylene glycol monobutyl ether, for example.

After the reaction is completed, the resultant reaction product is separated from the reaction mixture by following the conventional procedure. From the separated product, the thiazolidine-2,4-dione compound represented by the general formula I can be obtained by subjecting the methoxymethyl group of the reaction product to a reaction by the conventional procedure for denuding the methoxymethyl group of protection in the presence of an acid such as hydrochloric acid, nitric acid, phosphoric acid, formic acid, acetic acid, or propionic acid.

The thiazolidine-2,4-dione compound of this invention is effective in curing various complications of diabetes as with cataract, retinopathy, neurotic disorder, and renal disorder Though the dosage of this compound to be used as a medicine is variable with the symptom, the daily dose is generally in the range of from 1 to 100 mg, preferably from 5 to 50 mg per adult. This daily dose is desired to be administered either wholly at once or as divided in two or three portions, depending on the sympsom. As respects the manner of administration, the medicine may be used in a desired form fit for administration. Though the oral administration is particularly desirable, the administration by intravenous injection is permissible.

The medicine of this invention for the cure of a diabetic complication is characterized by containing the aforementioned thiazolidine-2,4-dione compound.

The medicine of this invention for the cure of a diabetic complication can be used in a varying form which is produced by mixing the aforementioned thiazolidine-2,4-dione compound with an efficaceous component or mixing this compound as one efficaceous component with a pharmaceutical carrier or an excipient and preparing the resultant mixture in the form of tablet, sugar-coated tablet, powder, capsule, granules, suspension, emulsion, or injection. The compounds which are effectively usable as a carrier or an excipient include calcium carbonate, calcium phosphate, starch, grape sugar, milk sugar, dextrin, alginic acid, mannitol, talc, and magnesium stearate, for example. The amount of the carrier or excipient to be used is in the range of from 0 to 99 times, preferably from 0 to 10 times, the weight of the thiazolidine-2,4-dione compound represented by the general formula I.

Now, the present invention will be described more specifically below with reference to working examples.

EXAMPLE 1

A solution of 15 g of p-aminoacetophenone in 300 ml of acetone was combined with 70 ml of water and 31 ml of 12N hydrochloric acid and the resultant mixture was stirred for 30 minutes with 21 ml of an aqueous solution containing 10.11 g of sodium nitrite added dropwise in advance thereto at 5° C. The produced reaction solution and 87.6 ml of ethyl acrylate added dropwise thereto and 1.59 g of copper (I) oxide added piecemeal thereto at 40° C. were stirred for 1.5 hours. The resultant mixture was combined with water, extracted from ethyl acetate, washed with a saturated aqueous saline solution, dried with anhydrous magnesium sulfate, and distilled under a vacuum to expel the solvent. The residue of the distillation was subjected to flush column chromatography. From the ethyl acetate-n-hexane (1:10) fraction of the eluate, 21.35 g of ethyl-2-chloro-3-(4-acetylphenyl)propionate aimed at was obtained.

A solution of 11.16 g of ethyl-2-chloro-3-(4-acetylphenyl)propionate in 190 ml of ethanol and 3.34 g of thiourea and 3.60 g of sodium acetate added thereto were refluxed by heating for a whole day and night. The refluxed mixture was distilled under a vacuum to expel the solvent. The residue of the distillation was combined with water, filtered, and washed with water. The produced residue and 2N hydrochloric acid added thereto were refluxed by heating for 2.5 hours. The refluxed mixture was neutralized with sodium hydrogen carbonate as kept cooled with ice and extracted from ethyl acetate. The ethyl acetate layer was washed sequentially with water and a saturated aqueous saline solution, dried with anhydrous magnesium sulfate, and then distilled under a vacuum to expel the solvent. The resultant residue was subjected to flush column chromatography. From the ethyl acetate-n-hexane (1:2) fraction of the eluate, 5.46 g of 5-(4-acetylbenzyl)thiazolidine-2,4-dione aimed at was obtained. A solution of 5.44 g of 5-(4-acetylbenzyl)thiazolidine-2,4-dione and 5.89 g of 3,4-dimethoxymethoxybenzaldehyde in 106 ml of a methanol 10% potassium hydroxide solution was stirred at room temperature for a whole day and night. The resultant mixture was neutralized with 6N hydrochloric acid as kept cooled with ice and distilled under a vacuum to expel methanol The residue of this distillation was combined with water and extracted from ethyl acetate. The ethyl acetate layer was washed with a saturated saline solution, dried with anhydrous magnesium sulfate, and distilled under a vacuum to expel the solvent The produced residue was subjected to flush column chromatography. From the ethyl acetate-n-hexane (1:2) fraction of the eluate, 4.47 g of 5-{4-3-(3,4-dimethoxymethoxyphenyl)-2-propenoyl]benzyl} thiazolidine-2,4-dione was produced.

A solution of 4.47 g of 5-{4-3-(3,4-dimethoxymethoxyphenyl-2-propenoyl]benzyl}thiazolidine-2,4-dione in 30 ml of methanol and 30 ml of tetrahydrofuran and 30 ml of 6N hydrochloric acid added thereto were stirred at 60° C. for three hours. The resultant mixture was neutralized with sodium hydrogen carbonate as kept cooled with ice and distilled under a vacuum to expel the solvent. The produced residue was combined with methanol and filtered. The filtrate was concentrated under a vacuum. The resultant concentrate was subjected to flush column chromatography. From the chloroform-methanol (20 1) fraction of the eluate, 1.55 g of 5-4-3-(3,4-dihydroxyphenyl)-2-propenoyl]benzyl} thiazolidine-2,4-dione (Compound 1) was obtained. The NMR data of this compound support the structure of Formula IV.

NMR (CDCl₃, DMSO-d₆, TMS): δ(ppm)
3.05~3.52 (2 H,m),
4.57 (1 H, double d, J=9 and 4 Hz), 6.68~8.12 (9 H,m).

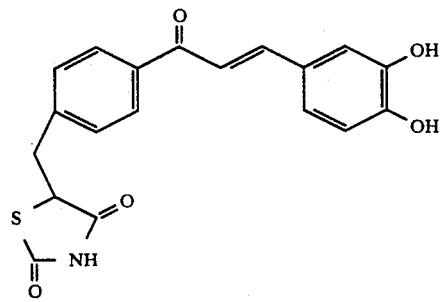

EXAMPLE 2

From 5 g of 5-(4-acetylbenzyl)thiazolidine-2,4-dione and 4.72 g of 3-methoxy-4-methoxymethoxybenzaldehyde, 6.20 g of 5-{4-[3-(3-methoxy-4-methoxymethoxyphenyl)-2-propenoyl]benzyl}thiazolidine-2,4-dione was obtained by following the procedure of Example 1. This product was subjected to the same reaction as in Example 1 to produce 3.74 g of 5-{4-[3-(4-hydroxy-3-methoxyphenyl)-2-propenoyl]benzyl}thiazolidine-2,4-dione (Compound 2) was obtained. The NMR data of this compound support the structure of Formula V.

NMR (CDCl₃, DMSO-d₆, TMS): δ(ppm)
3.05~3.52 (2 H,m),
4.57 (1 H, double d, J=9 and 4 Hz), 6.68~8.12 (9 H,m).

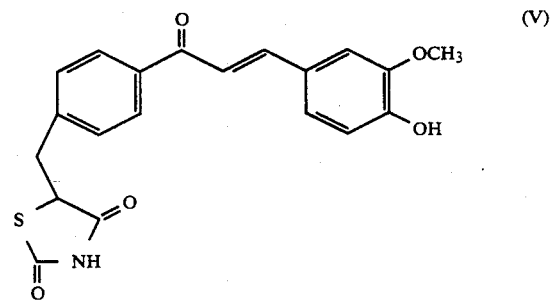

EXAMPLE 3 solution of 5 g of m-aminoacetophenone in 100 ml of acetone was combined with 25 ml of water and 15 ml of 47% hydrobromic acid and the resultant mixture was stirred for 30 minutes with 10 ml of an aqueous solution containing 3.32 g of sodium nitrite added dropwise in advance thereto at 5 C. The produced reaction solution and 28 ml of ethyl acrylate added dropwise thereto and 0.53 g of copper (I) oxide added piecemeal thereto at 40° C. were stirred for 2 hours. The resultant mixture was combined with water, extracted with ethyl acetate An organic layer was washed with water and a saturated aqueous saline solution, dried with anhydrous magnesium sulfate, and distilled under a vacuum to expel the solvent to obtain ethyl 2-bromo-3-(3-acetylphenyl)propionate.

A solution of ethyl 2-bromo-3-(3-acetylphenyl)propionate in 150 ml of ethanol and 2.67 g of thiourea and 3.03 g of sodium acetate added thereto were refluxed by heating for 5 hours. The refluxed mixture was distilled under a vacuum to expel the solvent. The residue of the distillation was combined with water, extracted with chloroform, washed with water and a saturated aqueous saline solution, and dried with anhydrous magnesium sulfate. The produced residue and 2N hydrochloric acid added thereto were refluxed by heating for 3 hours. The refluxed mixture was cooled and extracted with ethyl acetate. The ethyl acetate layer was washed sequentially with water and a saturated aqueous saline solution, dried with anhydrous magnesium sulfate, and then distilled under a vacuum to expel the solvent. The resultant residue was subjected to flush column chromatography. From the ethyl acetate-n-hexane (1:1) fraction of the eluate, 4.90 g of 5-(3-acetylbenzyl)thiazolidine-2,4-dione aimed at was obtained. A solution of 25.0 g of 5-(3-acetylbenzyl)thiazolidine-2,4-dione and 19.7 g of 3-methoxy-4-methoxymethoxybenzaldehyde in 400 ml of a methanol 10% potassium hydroxide solution was stirred at room temperature for 2.5 hours. The resultant mixture was neutralized with 2N hydrochloric acid as kept cooled with ice and distilled under a vacuum to expel methanol. The residue of this distillation was combined with water and a saturated saline solution and extracted with ethyl acetate. An organic layer was washed with water and the saturated saline solution, dried with anhydrous magnesium sulfate, and distilled under a vacuum to expel the solvent. The produced residue was subjected to flush column chromatography. From the ethyl acetate-n-hexane (2:1) fraction of the eluate, 23.1 g of 5-3-[3-(3-methoxy-4-methoxymethoxyphenyl)-2-propenoyl]benzyl}thiazolidine-2,4-dione was produced.

The resultant concentrate was subjected to flush column chromatography by a similar method to Example 1. From the chloroform-methanol (20:1) fraction of the 13.6 g of 5-{3-[3-(4-hydroxy-3-methoxyphenyl)-2-propenoyl]benzyl}thiazolidine-2,4-dione (Compound 3) was obtained. The NMR data of this compound support the structure of Formula VI.

NMR (CDCl₃, TMS): δ(ppm)
3.05~3.73 (2 H,m), 3.88 (1 H,s),
4.51 (1 H, d d, J=9 and 4 Hz), 6.68~6.98 (9 H,m).

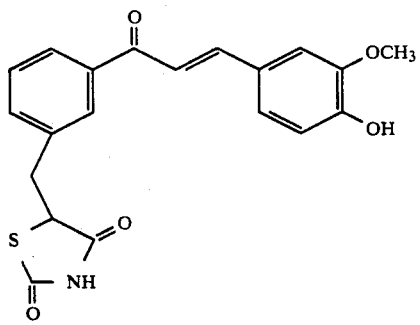

(VI)

TEST EXAMPLE 1

Determination of Aldose Reductase-inhibiting Activity

A five-week old Wistar type male rat was sacrificed under anesthesia and immediately dissected to remove crystalline lens. From the crystalline lens, aldose reductase was prepared by following the Hyman et al's method [J. Biol. Chem., 240, 877-882 (1965)] with necessary modifications.

The aldose reductase activity was determined by the Dufrane et al's method [Biochem. Med., 32, 99-105 (1984)].

In 400 μl of a 135 mM sodium-potassium phosphate buffer solution (pH 7.0) prepared in advance so as to contain 100 mM lithium sulfate, 0.03 mM NADPH (reducing type nicotinamide adenine dinucleotide phosphate), and 0.1 mM DL-glyceraldehyde as a substrate, 50 μl of the aforementioned aldose reductase and 50 μl of a sample of a varying concentration (having Compound 1, or Compound 2, or Compound 3 dissolved in ethanol) added thereto were left reacting at 30° C. for 30 minutes. Then, the reaction was stopped by addition of 0.15 ml of 0.5N hydrochloric acid. The NADP (oxide type nicotinamide adenine dinucleotide phosphate) produced by the reaction in the reaction mixture was converted into a fluorescent substance by the addition thereto of 0.5 ml of 6N sodium hydroxide containing 10 mM imidazole. After the elapse of 60 minutes following the conversion, the produced reaction mixture was tested for intensity of fluorescence. The intensity of fluorescence was determined by the use of a fluorescence tester (produced by Corona Denki K.K. and marketed under trademark designation of "MTP-100F Corona Microplate Reader") under the conditions of 360 nm of excitation wavelength and 460 nm of fluorescent wavelength. The intensity of fluorescence determined by repeating the procedure described above, except ethanol was added in the place of the sample was used as a control value. As the aldose reductase inhibiting activity of a sample, the concentration of the sample required for inhibiting 50% of the aldose reductase activity due to a decline of the intensity of fluorescence (i.e. 50% inhibition concentration: $IC_{50}$ value) was obtained. The results are shown in Table 1.

TABLE 1

| Compound No. | 50% inhibition concentration (M) |
| --- | --- |
| 1 | $5.2 \times 10^{-7}$ |
| 2 | $4.2 \times 10^{-6}$ |
| 3 | $1.9 \times 10^{-6}$ |

TEST EXAMPLE 2

Action to Curb Accumulation of Sorbitol in Red Blood Cells

Groups each of five three-week old Wistar type male rats were used for the test. To the rats, streptozotocin was administered at a concentration of 65 mg/kg via the tail vein. Of these rats, those whose blood sugar values fell in the range of from 250 to 650 mg/dl one week after the administration were designated as diabetic rats. As a control medicine, Compound 4 represented by the formula VII was used.

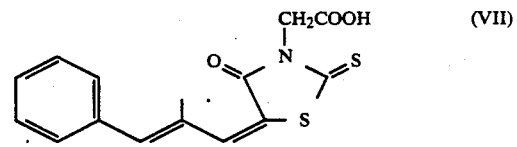

(VII)

The five groups, i.e. the group of untreated diabetic rats, the group of rats subjected to administration of control medicine (50 mg/kg×2/day), the group of rats subjected to administration of sample (100 mg/kg/day), and the group of normal rats, were tested. A given medicine was suspended in 5% gum arabic and orally administered continually for four days after the elapse of two weeks following the onset of diabetes. To the group of untreated diabetic rats and the group of normal rats, a 5% gum arabic solution of a given medicine was administered in a ratio of 10 ml/kg. After the elapse of three hours following the administration, the blood was extracted from each rat with the aid of heparin via the tail vein (for the determination of blood sugar) and the abdominal aorta.

The red blood cells were separated from the blood extracted with heparin and washed three times with a physiological saline solution at 4° C. to obtain packed red cells (PRC).

The PRC was tested for sorbitol content by the Malon et al's method [Diabetes, 29, 861-864 (1980)]. The determination of the blood sugar value was carried out by the alucose-oxidase method.

The blood sugar drop ratio and the sorbitol accumulation inhibition ratio were calculated in accordance with Formula 1 and Formula 2. The results are shown in Table 2.

TABLE 2

| Compound No. | Blood sugar dropratic (%) | Sorbitol accupalation inhibition ratio (%) |
|---|---|---|
| 1 | 46.8 | 79.1 |
| 2 | 60.5 | 93.8 |
| 3 | 42.6 | 95.6 |
| 4 | 7.2 | 90.3 |

Formula 1

Blood sugar drop ratio (%)=(1−[(Average blood sugar value of the group of rats subjected to administration of sample or control medicine−Average blood sugar value of the group of normal rats)/(Average blood sugar value of the group of untreated diabetic rats−Average blood sugar value of the group of normal rats)])×100

Formula 2

Sorbitol accumulation inhibition ratio (%)=(1−[Average sorbitol value of the group of rats subjected to administration of sample or control medicine−Average sorbitolvalue of the group of normal control rats)/(Average sorbitol value of the group of untreated diabetic rats−Average sorbitol value of the group of normal control rats)])×100

TEST EXAMPLE 3

Acute Toxicity

The compounds 1, 2 and 3 of this invention were tested for acute toxicity by oral administration thereof to ICR type male mice (five-week old). Their $LD_{50}$ values were found to be not less than 1,000 mg/kg, indicating that their safety is high as compared with the efficaceous dosage.

What is claimed is:

1. A method for inhibiting aldose reductase, said method comprising administering an effective amount of the thiazolidine-2,4-dione compound represented by formula I

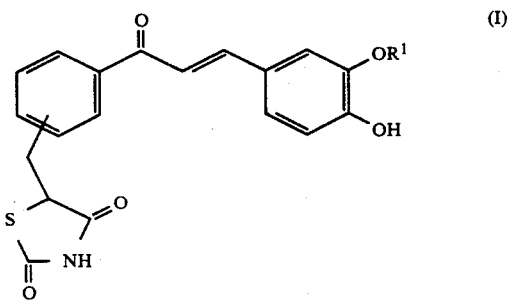

wherein $R^1$ is a hydrogen atom or a methyl group to inhibit aldose reductase to a patient in need of such inhibition.

2. The method according to claim 1, wherein said compound is 5-{4-[3-(3,4-dihydroxyphenyl)-2-propenoyl]benzyl}thiazolidine-2,4-dione.

3. The method according to claim 1, wherein said compound is 5-{5-[3-4-hydroxy-3-methoxyphenyl)-2-propenyl]phenylmethyl}thiazolidine-2,4-dione.

4. The method according to claim 1, wherein said compound is 5-{3-[3-(3,4-dihydroxyphenyl)-2-propenoyl]benzyl}thiazolidine-2,4-dione.

5. The method according to claim 1, wherein said compound is 5-{3-[(4-hydroxy-3-methylphenyl)-2-propenoyl]benzyl}thiazolidine-2,4-dione.

6. The method according to claim 1, wherein said compound is 5-{2-[3-(3,4-dihydroxyphenyl)-2-propenoyl]benzyl}thiazolidine-2,4-dione.

7. The method according to claim 1, wherein said compound is 5-{2-[3-(4-hydroxy-3-methylphenyl)-2-propenoyl]benzyl}thiazolidine.

* * * * *

UNITED STATES PATENT AND TRADEMARK OFFICE
CERTIFICATE OF CORRECTION

PATENT NO. : 5,225,426
DATED : July 6, 1993
INVENTOR(S) : Shozo MIYAOKA et al

It is certified that error appears in the above-indentified patent and that said Letters Patent is hereby corrected as shown below:

In Column 3, line 34, delete "2propenoyl]benzyl}" and insert
-- 2-propenoyl]benzyl} --.
In Column 4, line 17, delete "disorder" and insert -- disorder. --.
In Column 5, line 58, delete "(20 1)" and insert -- (20:1) --.

Signed and Sealed this

Fifth Day of April, 1994

Attest:

BRUCE LEHMAN

Attesting Officer

Commissioner of Patents and Trademarks